United States Patent [19]

Duggan et al.

[11] Patent Number: 4,652,542
[45] Date of Patent: Mar. 24, 1987

[54] RUTHENIUM-COBALT CARBONYL CATALYSTS FOR THE DEALKOXYHYDROXYMETHYLATION OF ACETALS TO FORM GLYCOL ETHERS

[75] Inventors: D. Michael Duggan, Drexel Hill; Harry K. Myers, Jr., Cochranville; James E. Lyons, Wallingford, all of Pa.

[73] Assignee: Sun Refining and Marketing Company, Philadelphia, Pa.

[21] Appl. No.: 782,805

[22] Filed: Oct. 2, 1985

Related U.S. Application Data

[63] Continuation-in-part of Ser. No. 622,817, Jun. 21, 1984, abandoned.

[51] Int. Cl.$^4$ ............................................. B01J 31/12
[52] U.S. Cl. .................................... 502/154; 502/161
[58] Field of Search ................................ 502/154, 161

[56] References Cited

U.S. PATENT DOCUMENTS

| | | | |
|---|---|---|---|
| 4,062,898 | 12/1977 | Dubeck et al. | 260/632 B |
| 4,346,020 | 8/1982 | Pretzer et al. | 252/429 R |
| 4,390,734 | 6/1983 | Knifton | 568/678 |

*Primary Examiner*—W. J. Shine
*Attorney, Agent, or Firm*—J. Edward Hess; Donald R. Johnson; Stanford M. Back

[57] ABSTRACT

The cobalt carbonyl catalyst $R^5CCo_3(CO)_9$, desirably with $Ru_3(CO)_{12}$, wherein $R^5$ is hydrogen; alkyl, preferably $C_{1-5}$ lower alkyl; cycloalkyl or substituted cycloalkyl; cycloalkenyl, such as cyclohexenyl or cyclooctenyl; $C_{1-12}$ alkoxy, such as methoxy or propoxy; aryl or alkyl-, cycloalkyl-, alkoxy-, halo-, or cyano-substituted aryl; cyano; or a silyl carbyne moiety of the formula $R_3^6Si$, wherein $R^6$ is alkyl or aryl, effectively catalyzes the dealkoxyhydroxymethylation of aldehyde acetals to form glycol monoethers. Methylal, for example, may be reacted with syngas; i.e., CO and $H_2$, in the presence of this catalyst system to form the corresponding ethylene glycol monomethyl ether.

4 Claims, No Drawings

RUTHENIUM-COBALT CARBONYL CATALYSTS FOR THE DEALKOXYHYDROXYMETHYLATION OF ACETALS TO FORM GLYCOL ETHERS

CROSS REFERENCE TO RELATED APPLICATION

This application is a continuation-in-part of Ser. No. 622,817, filed June 21, 1984, now abandoned.

BACKGROUND OF THE INVENTION

1. Scope of the Invention

This invention relates to the dealkoxyhydroxmethylation of aldehyde acetals. More particularly, it relates to a novel process for the dealkoxyhydroxymethylation of certain dialkyl-, dicycloalkyl-, diaryl-, or cyclic-aldehyde acetals by reacting said acetals with syngas, i.e., hydrogen and carbon monoxide, in the presence of carbyne-substituted cobalt carbonyl catalysts, desirably in combination with a ruthenium carbonyl compound, to form the corresponding glycol monoethers. The acetals described herein may be prepared separately or formed in situ from the corresponding aldehyde and alcohol precursors. This invention also relates to certain novel ruthenium carbonyl-carbyne-substituted cobalt carbonyl catalyst compositions per se.

The glycol ethers described herein encompass known classes of compounds having various uses, as for example as jet fuel additives, cleaners, coatings, solvents, intermediates in the production of certain diphthalates, and the like.

2. Description of the Prior Art

One current well-known method of manufacturing glycol monoethers such as monoalkyl ethers consists of reacting ethylene oxide with the alcohol corresponding to the desired alkyl ether, employing various known catalyst systems.

Alternatively, the cobalt-catalyzed reaction of aldehydes or their dialkyl acetals with syngas, i.e., a carbon monoxide-hydrogen mixture, to form the corresponding glycol ether is also described in the art. Thus, for example, a method of making ethylene glycol ethers is described in U.S. Pat. No. 2,525,793 which employs cobalt oxide to catalyze the reaction of methylal with syngas to provide a reaction mixture which, after hydrogenation over nickel, gives relatively uneconomical conversions on the order of 25–33%.

Numerous attempts have been made to obtain more practical yields of glycol ethers from aldehydes or their dialkyl acetals. A number of promoters have been used in conjunction with various cobalt catalysts in an effort to improve reaction rates and product yields. U.S. Pat. No. 4,062,898, for example, discloses a ruthenium chloride-promoted cobalt iodide catalyst which hydrocarbonylates formaldehyde dimethylacetal (methylal) to ethylene glycol monomethyl ether (EGMME) in yields of 10% or less. The reaction temperature required is 185° C. at 20 atm. or above. A second method, described in Jpn. Kokai Tokkyo Koho 81 83,432 (1981) uses substantial quantities of 2,4,6-collidine or similar aromatic amines to promote the cobalt carbonyl-catalyzed hydrocarbonylation of methylal in benzene as a solvent. The reaction of methylal with highly pressurized syngas in this process at 190° C. for 10 hours gave 44% selectivity to EGMME at 98% conversion. A further patent, Euro. Pat. Appln. EP No. 34,374 (1981) uses both iodine and triphenyl or tricyclohexylphosphine together with $RuCl_3.H_2O$ to promote the $Co(Ac)_2.4-H_2O$ - catalyzed hydrocarbonylation of methylal using 3000 psig of syngas, and temperatures of between 150° and 175° C. to obtain results nearly comparable to those of the Japanese.

More recently, Knifton has found that cobalt carbonyl promoted with a Group VIB donor ligand catalyzes the hydrocarbonylation of an aldehyde in an alcohol to make ethylene glycol monoethers; U.S. Pat. No. 4,308,403. Yields of ethylene glycol monobutyl ether (EGMBE) as high as 61 wt. % were reported in this patent. A cyclopentadienyl-ligated cobalt catalyst is also effective for these reactions giving glycol ethers in up to 54% yield; U.S. Pat. No. 4,317,943.

Propylene glycol monoalkyl ethers are formed by contacting high pressure mixtures of carbon monoxide and hydrogen with either an acetal or an aldehyde and an alcohol using a cobalt catalyst promoted with a tin- or germanium-containing compound; U.S. Pat. No. 4,356,327. Yields of glycol ethers up to 31 wt. % were reported in this patent. Ethylene glycol ethers were also formed from a formaldehyde acetal or formaldehyde and an alcohol using tin or germanium promoters for cobalt carbonyl; U.S. Pat. No. 4,357,477. The highest gycol ether yield (EGMBE) was 53% in this case.

Further, propylene glycol monoalkyl ethers were formed by hydrocarbonylation of acetaldehyde acetals or acetaldehyde and alcohols using rhodium, ruthenium or nickel compounds to promote either cobalt carbonyls or cobalt compounds having group V ligand systems attached. Glycol ether yields up to 28 wt. % were realized when these promoters were used; Knifton, U.S. Pat. No. 4,390,734 (1983).

Thus, the use of various promoters for the cobalt-catalyzed hydrocarbonylation of aldehydes or acetals has resulted in glycol ether yields of from 10–61 wt. %, depending on the glycol ether produced. The highest reported yield of EGMME is 44%, of EGMBE is 61% and propylene glycol monoethyl ether, PGMEE is 28%.

SUMMARY OF THE INVENTION

In accordance with the present invention, there is provided an improved process for the reaction of certain dialkyl-, dicycloalkyl-, diaryl-, or cyclic-aldehyde acetals or their aldehyde-alcohol precursors, with syngas in the presence of a carbyne-substituted cobalt carbonyl catalyst, $R^5CCo_3(CO)_9$, wherein $R^5$ may be hydrogen; alkyl, preferably $C_{1-12}$ alkyl, and most preferably $C_{1-5}$ lower alkyl; cycloalkyl or alkyl-substituted cycloalkyl, preferably $C_{5-10}$ moieties; cycloalkenyl, such as cyclohexenyl or cyclooctenyl, preferably $C_{6-12}$ cycloalkenyl; alkoxy, such as methoxy or propoxy, preferably $C_{1-12}$ alkoxy; aryl or alkyl-, cycloalkyl-, alkoxy-, halo-, or cyano-substituted aryl, preferably $C_{6-20}$ moieties; cyano; or a silyl moiety of the formula $R_3^6Si$ wherein $R^6$ is alkyl or aryl, to form the corresponding glycol monoethers.

In a further, and preferred, embodiment of this invention it has been found that when the aforedescribed $R^5CCo_3(CO)_9$ catalyst is combined with the ruthenium carbonyl catalyst $Ru_3(CO)_{12}$, the selectivity for the desired glycol ether is significantly increased.

The process of this invention, which may best be described as the dealkoxyhydroxymethylation of an acetal, formed separately or in situ by the reaction of an aldehyde with an alcohol, may be depicted by the following general reaction scheme:

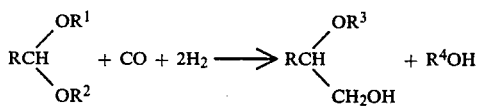

wherein R is hydrogen, alkyl, cycloalkyl, or aryl; $R^1$ and $R^2$, which may be the same or different, are alkyl, cycloalkyl, or aryl, and taken together may form a cyclic acetal; $R^3$ is alkyl, cycloalkyl, aryl, or an hydroxy-substituted hydrocarbon moiety; and $R^4$ is alkyl, cycloalkyl, or aryl corresponding to whichever $R^1$ or $R^2$ group is displaced. In the case where cyclic acetals are employed, however, no alcohol by-product is formed.

Examples $R^1$, $R^2$, $R^3$ or $R^4$ alkyl, cycloalkyl, and aryl groups which may be employed include such substituted or unsubstituted groups as:

(a) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;

(b) substituted or unsubstituted cycloalkyl groups, preferably those having from about 5 to about 20 carbon atoms, such as cyclopentyl, cyclohexyl, cycloheptyl, 3-methylcyclopentyl, 3-butylcyclohexyl, cyclooctyl, adamantyl, decalyl, 3-phenylcycloheptyl and the like; and (c) substituted or unsubstituted aryl groups, preferably those having 6 to about 20 carbon atoms such as benzyl, phenyl, naphthyl, fluoranthyl, tetralyl, tolyl, ethylphenyl, cumyl, anisyl, chlorophenyl, and the like.

It will be understood that when $R^1$ and $R^2$ in the foregoing reaction scheme are different, the resulting product will actually be mixtures of the corresponding glycol ethers and alcohols. It will also be understood, as mentioned above, that $R^1$ and $R^2$ may be joined by one or more bridging atoms to form a cyclic acetal, in which case, under the conditions of this reaction the heterocyclic ring will cleave at a carbon-oxygen bond of the acetal moiety, and hydroxymethylate, thereby forming a dihydroxy compound, i.e. an hydroxy-substituted glycol ether.

This process provides an improvement over the methods of the prior art in that the instant catalysts do not require the added presence of the iodide, amines, or phosphine promoters such as are disclosed in the prior art, and thus are less costly and easier to prepare and recover. Moreover, these novel catalysts permit the reaction to be carried out under mild conditions of time and temperature, yet most surprisingly provide rates and selectivities of desired product over those obtained by the use of cobalt carbonyl alone.

DESCRIPTION OF THE PREFERRED EMBODIMENTS

The carbyne-substituted catalyst of this invention, $R^5CCo_3(CO)_9$, wherein $R^5$ is as defined above, may be prepared in accordance with the procedures taught in *Inorganic Synthesis*, Wiley-Interscience Pub., New York, Vol. 20, #53-B, pp. 226 et seq. (1980). As stated above, this catalyst may be used with $Ru_3(CO)_{12}$, a known compound. When used in combination, the molar ratios of these two components should optimally be in the range of about 10:1 to 1:10, and preferably about 5:1 to 1:5.

The acetal dealkoxyhydroxymethylation reaction with syngas, utilizing the catalysts of this invention, may conveniently be conducted in a generally known manner whereby the desired acetal is reacted with syngas under elevated temperature and pressures for given periods of time, during which period the reaction mixture is actively stirred. In this reaction, the volume ratio of carbon monoxide to hydrogen in the syngas desirably is in the range of from about 1:5 to 5:1, and more preferably 1:3 to 3:1. Following rapid cooling, the reaction product is then recovered from the mixture in a routine manner. In contrast to prior art reaction conditions described above, the catalysts of this invention advantageously permit the use of mild operating conditions. Thus, temperatures in the range of from about 100° to 200° C., and preferably about 125° to 175° C., pressures of from about 500 to 5000 psi, and preferably about 1000 to 3000 psi, may satisfactorily be employed. The reaction time is not critical, and may range up to several hours, desirably up to 5-6 hours.

The weight ratio, in grams, of catalyst mixture to acetal, is desirably in the range of from about 1:1000-10:1, and preferably in the range of from about 1:100-1:1 in a batch reaction.

In a further embodiment of this invention, it has been found that highly advantageous effects may also be obtained in this dealkoxyhydroxymethylation process by the use of solvents with the acetal. The solvents which may be advantageously used comprise any polar or non-polar organic solvents which are inert to the conditions of the reaction. Included amongst these solvents are $C_{1-12}$ alcohols, such as methanol, ethanol, butanol, 3-ethyl-2-hexanol and the like; ethers which will not cleave under the conditions of the reaction, such as glyme, diglyme, diphenyl ether and the like; aromatics and substituted aromatics such as benzene, toluene, xylene, chlorobenzene, dichlorobenzene, anisole, and the like.

The solvents may be employed in amounts of up to 90 volume percent of the reaction mixture, and preferably in amounts of from about 20 to 80 percent.

In still a further embodiment of this process, it has been found that with acyclic acetals, when the reaction is carried out in an excess of an alcohol solvent, wherein the ratio of acetal to alcohol solvent is desirably in the range of from about 1:2 to 1:20, and preferably 1:5 to 1:10, and wherein the R group of the alcohol used is different from the $R^1$ and/or $R^2$ substituents on the acetal starting material, these different R groups of the alcohol will, in the course of the reaction, replace the $R^1$ and/or $R^2$ groups on the acetal in a substitution reaction, thereby resulting in a glycol monoether in which the R group of the ether moiety corresponds to the R group of the alcohol solvent.

This reaction may be illustrated by the following equation:

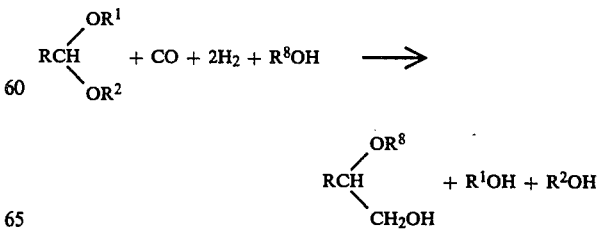

wherein R, $R^1$, and $R^2$ are as defined above except that cyclic acetals are not included, and $R^8$ is a different alkyl, cycloalkyl, or aryl group than $R^1$ and/or $R^2$, and desirably has from 1 to about 20 carbon atoms. Depending upon the length of time the reaction is allowed to continue, intermediate mixtures of higher and lower molecular weight substituents on the acetal corresponding to both those of the $R^1$ and/or $R^2$ groups and those of the alcohol solvent will be found in the reaction product.

The acetal starting materials employed in this invention have the aforedescribed general formula, namely

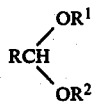

wherein R, $R^1$, and $R^2$ are as defined above. These acetals can be prepared in a known manner, separately or in situ, as for example as described in E. V. Dehmlav and J. Schmidt, Tetrahedron Letters, p.95–6 (1976) B. S. Bal and H. W. Pinnick, J. Org. Chem., V44 (21), p. 3727–8 (1979) D. W. Hall, U.S. Pat. No. 3,492,356, Jan. 27, 1970, by the reaction of an aldehyde such as formaldehyde with an alcohol, or mixture of alcohols, of the general formula $R^1OH$ or $R^2OH$, where again $R^1$ and $R^2$ are as defined above, to form the corresponding acetal. In the case of cyclic acetals, the alcohol must be diol. Hereinafter, when the acetal is referred to, it will be understood that the corresponding precursors, i.e., the desired aldehyde and alcohol, are also intended to be included. As mentioned above, the $R^1$ and $R^2$ substituents of the acetal may comprise a bridging group to form such cyclic acetals as:

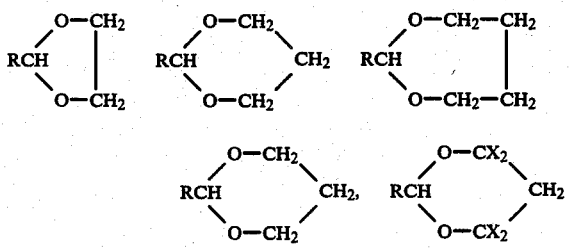

and the like, wherein R is as defined above, and wherein X is selected from the group consisting of alkyl, aralkyl, aryl and cycloalkyl groups, preferably those having from 1 to about 20 carbon atoms. As described above, cleavage of the ring under the conditions of this reaction will result in the formation of the corresponding hydroxy-substituted glycol ether.

Illustrations of products thus formed from cyclic acetals include, for example, diethylene glycol from dioxolane, the conversion of 2- or 4-methyldioxolane to the corresponding hydroxy glycol ether, and the like.

It is important, in selecting the acetal starting material, that it not contain any substituents which would adversely affect the reaction. In other words, the R, $R^1$, and $R^2$ groups should not, for example, contain such reactive moieties as phosphine, arsine, amino, sulfido or carbonyl groups, acetal moieties, or olefins or acetylenic triple bonds. Other like groups will be recognized or readily determined by thos skilled in the art of resulting in products other than the desired monoethers. On the other hand, halogen, alkoxy, and hydroxy moieties and the like may be present on the hydrocarbon substituents without adverse effect.

When these acetals are dealkoxyhydroxymethylated with syngas in accordance with the process of this invention, there is obtained the corresponding glycol monoether in which the ether moiety will correspond to the $R^1$ and $R^2$ groups of the acetal starting material. Also formed in lesser amounts are a tri-substituted ethane of the general formula

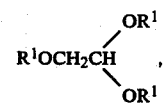

wherein $R^1$ (or alternatively, $R^2$, or mixtures of $R^1$ and $R^2$) is as defined above, which may be recycled to form additional acetal starting material, and alcohol by-products. Again, as above, if the $R^1$ and $R^2$ groups of the acetal are different, a mixture of corresponding R-substituted compounds will result. This tri-substituted ethane is believed to form during the reaction from an alkoxyacetaldehyde, e.g., the intermediate methoxy acetaldehyde, when methylal is used, ethoxyacetaldehyde when ethylal is used, and the like.

As shown below, the selectivities for the desired monoether over the tri-substituted by-product are in the ratio of from abut 3:1 to as much as 10:1 or more.

In a preferred embodiment of this invention, the starting materials are preferably symmetrical acetals where the $R^1$ and $R^2$ groups are lower alkyl groups of 1 to about 4 carbon atoms, thereby forming the corresponding glycol mono-lower alkyl ethers such as the monomethyl ether, the monoethyl ether, the monobutyl ether, and the like.

Alternatively, the acetal may contain such $R^1$ and $R^2$ groups as naphthyl and phenyl. In the case of naphthyl, the reaction, e.g., of the formaldehyde acetal with syngas will provide 2-(2-naphthyloxy)ethanol, a known sedative, which in turn may be oxidized to the corresponding 2-naphthyloxyacetic acid, a plant growth hormone.

Likewise, the dealkoxyhydroxymethylation of, e.g., the formaldehyde acetal wherein $R^1$ and $R^2$ are phenyl will produce 2-phenoxy-ethanol, a topical antiseptic, which when oxidized, results in phenoxyacetic acid, a fungicide. Similarly, the formaldehyde acetal wherein $R^1$ and $R^2$ are 2,4,5-trichlorophenyl will yield, 2,4,5-trichlorophenoxyacetic acid, a herbicide. In a like manner, when $R^1$ and $R^2$ are p-nonylphenyl, P-nonylphenoxyacetic acid, a corrosion inhibitor and antifoaming agent in gasoline and cutting oils will be formed.

Each of the aforedescribed products may be recovered routinely by methods well known in the art.

The invention will now be illustrated by, but is not intended to be limited to, the following examples.

EXAMPLES

Examples 1–6

A series of runs was carried out in which the following general procedure was employed, using as the catalyst $R^5CCo_3(CO)_9$ alone, or promoted with $Ru_3(CO)_{12}$.

To a 300 ml stainless steel autoclave equipped with a magnedrive stirrer was charged: methylal, and catalyst. Carbon monoxide and hydrogen were admitted and the reaction mixture as rapidly heated to the desired temperature. The mixture was stirred for the designated time at reaction temperature after which the reactor was cooled by immersion in an ice bath. When the contents reached 25° C. the final pressure was recorded. After venting the gas the liquid was analyzed by GLPC.

The results are reported in Table I below. The specific reaction conditions, amounts, and the use of solvents are described in footnote (a) in this table.

TABLE I

METHYLAL DEALKOXYHYDROXYMETHYLATION[a]

| EXAMPLES | CATALYST USED, MMOLES | | | | YIELD EGMME[b] % | CONV. OF METHYLAL % |
| --- | --- | --- | --- | --- | --- | --- |
| | [HCCo$_3$CO)$_9$] | [C$_8$H$_{13}$CCo$_3$(CO)$_9$] | [PhCCo$_3$(CO)$_9$] | [Ru$_3$(CO)$_{12}$] | | |
| 1 | 0.5 | 0 | 0 | 0 | 17 | 92 |
| 2 | 0.5 | 0 | 0 | 0.5 | 44 | 80 |
| 3 | 0.5[c] | 0 | 0 | 0.5 | 47 | 73 |
| 4 | 0 | 0.5 | 0 | 0 | 20 | 63 |
| 5 | 0 | 0.5 | 0 | 0.5 | 42 | 79 |
| 6 | 0 | 0 | 0.5 | 0.5 | 35 | 63 |

[a] 285 mmoles of methylal reacted at 150° C. under 3000 psi of 2/1 syngas (H$_2$/CO = 2/1) for 5 hours
[b] (moles EGMME formed/moles methylal reacted) × 100
[c] Methylal dried over activated mole sieves before run

EXAMPLE 7

In accordance with the procedure of Example 2 except that formaldehyde diethyl acetal is used in place of methylal, the monoethyl ether of ethylene glycol is formed in good yield.

EXAMPLE 8

In accordance with the procedure of Example 2 except that formaldehyde dibutyl acetal is used in place of methylal, the monobutyl ether of ethylene glycol is formed in high yield.

EXAMPLE 9

In accordance with the procedure of Example 2 except that acetaldehyde diethyl acetal is used in place of methylal, the monoethyl ether of propylene glycol is formed as a major reaction product.

EXAMPLE 10

In accordance with the procedure of Example 9 except acetaldehyde, 285 mmoles, and ethanol, 470 mmoles, were used in place of acetaldehyde diethyl acetal, the monoethyl ether of propylene glycol was detected among the reaction products.

EXAMPLE 11

To a 110 ml rocking autoclave is charged HCCo(CO)$_9$ (0.5 mmole), Ru$_3$(CO)$_{12}$ (1.0 mmole), methylal (27 mmoles), butanol (18.2 mmoles), and mesitylene as an internal standard. Carbon monoxide (800 psig) is charged to the reactor followed by hydrogen to a total pressure of 3200 psig and the mixture rocked 150° C. for 6 hours. Standardized gc of the reaction mixture after cooling shows that the monobutyl ether of ethylene glycol is formed in good yield.

EXAMPLE 12

In accordance with the procedures of Example 2, except that the cyclic acetal dioxolane is used instead of methylal, diethylene glycol is produced as a reaction product.

What we claim is:

1. Composition comprising R$^5$CCo$_3$(CO)$_9$ and Ru$_3$(CO)$_{12}$, wherein R$^5$ is hydrogen, alkyl, cycloalkyl or alkyl-substituted cycloalkyl, cycloalkenyl, alkoxy, aryl or alkyl-, cycloalkyl-, alkoxy-, halo-, or cyano-substituted aryl, cyano, or a silyl moiety of the formula R$_3^6$Si, wherein R$^6$ is alkyl or aryl.
2. Composition of claim 1 wherein R$^5$ is hydrogen.
3. Composition of claim 1 wherein R$^5$ is cyclooctenyl.
4. Composition of claim 1 wherein R$^5$ is phenyl.

* * * * *